United States Patent [19]

Hounsfield

[11] 4,118,628

[45] * Oct. 3, 1978

[54] RADIOGRAPHIC APPARATUS WITH CORRECTION FOR RADIATION HARDNESS VARIATIONS

[75] Inventor: Godfrey Newbold Hounsfield, Winthorpe, England

[73] Assignee: EMI Limited, Hayes, England

[*] Notice: The portion of the term of this patent subsequent to Aug. 23, 1994, has been disclaimed.

[21] Appl. No.: 793,387

[22] Filed: May 3, 1977

Related U.S. Application Data

[63] Continuation of Ser. No. 668,045, Mar. 18, 1976, Pat. No. 4,044,260.

[30] Foreign Application Priority Data

Mar. 18, 1975 [GB] United Kingdom ............... 11131/75

[51] Int. Cl.² .............................................. A61B 6/02
[52] U.S. Cl. .................................. 250/445 T; 250/360
[58] Field of Search .................... 250/360, 320, 445 T

[56] References Cited

U.S. PATENT DOCUMENTS

| 3,866,047 | 2/1975 | Hounsfield ........................ 250/445 T |
| 3,881,110 | 4/1975 | Hounsfield et al. ............. 250/445 T |
| 4,044,260 | 8/1977 | Hounsfield ........................ 250/445 T |

*Primary Examiner*—Alfred E. Smith
*Assistant Examiner*—T. N. Grigsby
*Attorney, Agent, or Firm*—Cooper, Dunham, Clark, Griffin & Moran

[57] ABSTRACT

In a radiographic apparatus employing a fan-shaped spread of penetrating radiation the nature of the source can cause the energy spectrum of the radiation to be variable with position in the fan. Means are provided to modify output signals from the apparatus to correct for errors caused by such variations. The modifying factors required can be calculated or can be determined using a phantom body by a method which is described.

4 Claims, 3 Drawing Figures

RADIOGRAPHIC APPARATUS WITH CORRECTION FOR RADIATION HARDNESS VARIATIONS

This is a continuation, of application Ser. No. 668,045 filed Mar. 18, 1975 and now U.S. Pat. No. 4,044,260.

This invention relates to a method of and apparatus for constructing a respresentation of the variation of absorption of a planar slice of a body with respect to penetrating radiation such as X- or γ- radiation.

One method of, and apparatus for, constructing such a representation is described in U.S. Pat. No. 3,778,614. According to one example described in that specification a scanning movement is imparted to a suitable of radiation to provide a plurality of substantially parallel pencil beams of radiation at each of a plurality of inclinations in the plane of the slice. A suitable detector is scanned in a corresponding manner to provide a measure of the absorption suffered by each of the beams on passing through the body. These measurements of absorption are then processed by suitable means to provide a distribution of absorption coefficients for the planar slice. To provide the required plurality of beams the source and detector are reciprocated in the plane of the slice and orbited in steps about a common axis normal to that plane. The processing is such that the finally displayed distribution of absorption coefficients is the result of successive approximations.

The method and apparatus described in the aforesaid British Patent has proved to be successful for examining parts of the living body such as the head. However the arrangement for carrying out the scanning operation is relatively slow and a faster scanning rate is desirable for certain parts of the body. In United States application Ser. No. 476,300 describes a method and apparatus for the same purpose including a source arranged to provide a fan shaped spread of radiation in the plane of the slice and a detector means including a plurality of detectors disposed to detect the radiation transmitted along a set of paths in that fan. The fan is of angular spread sufficient to include the entire region of interest in the body to provide the required plurality of beans therefore the source and detector means are subjected solely to an orbital movement.

It is known that in producing a fan shaped spread of radiation from an X-ray target, for a purpose such as that described, there is a variation of the transmitted energy spectrum, i.e. a variation of "hardness" of the radiations across the spread of the fan. Since this can lead to variations of absorption of the X-rays it can lead further to errors in the required representation unless suitable steps are taken to compensate.

It is an object of the invention to provide a suitable means of compensation for such variation of the energy spectrum.

According to the invention there is provided radiographic apparatus including a source of a substantially planar fan shaped spread of radiation adapted to irradiate a planar section of the body of a patient, detectors sensitive to the radiation and disposed to receive radiation emergent from the body to provide output signals indicative of the intensity of the radiation received along respective paths within said spread, means for moving said source and detectors relative to said body to provide further output signals for paths at different dispositions in said section and processing circuit means for modifying said output signals to compensate, at least in part, for variations in the amplitude thereof resulting from variations in the energy spectrum of said radiation with angular position in the fan-shaped spread.

In order that the invention may be clearly understood and readily carried into effect an example thereof will now be described with reference to the accompanying drawings of which:

Figure 1:
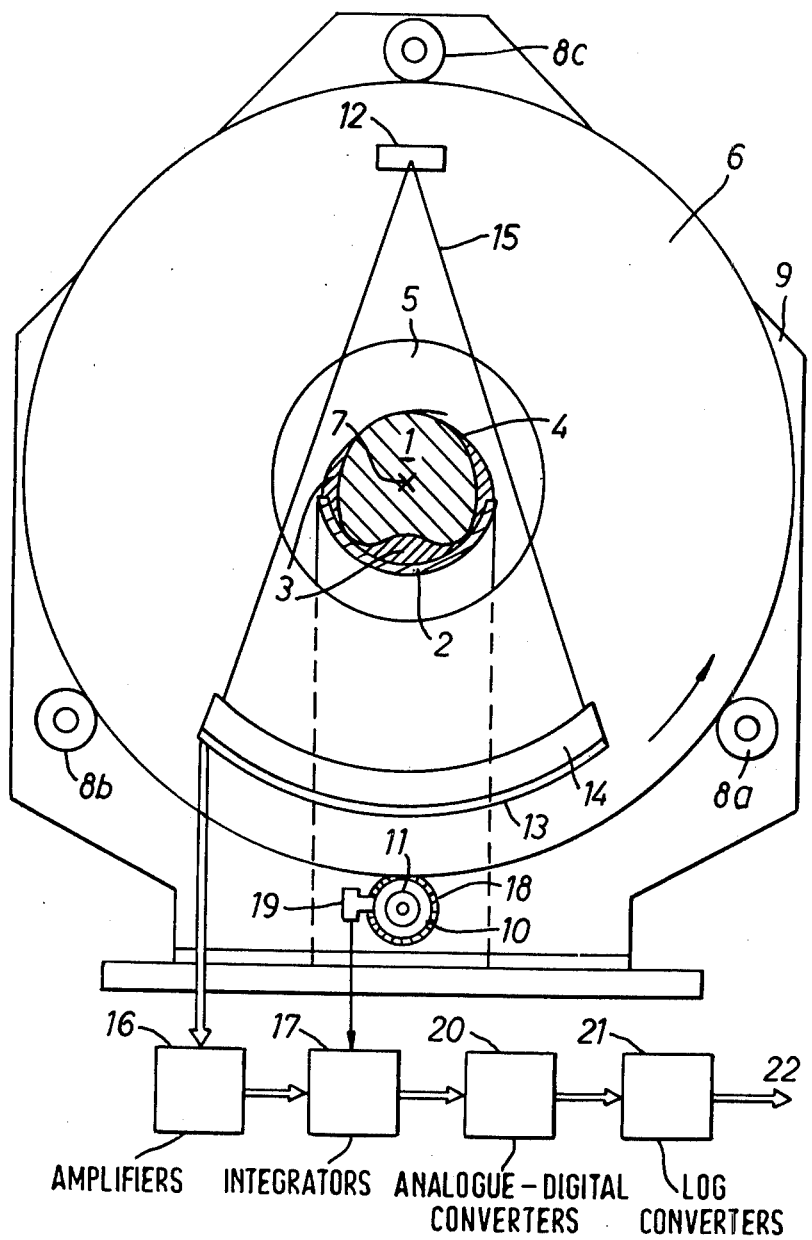
FIG. 1 shows a typical apparatus suitable for use with the inventions

Referring to FIG. 1 there is shown apparatus in accordance with one example of the invention. A body 1, of a patient to be examined, is shown in transverse section supported on a suitably shaped bed 2, also shown in transverse section. A material 3, having an absorption to the radiation similar to that of body tissue, is positioned between the body 1 and bed 2, partly to support the patient and partly to exclude air from the gap therebetween, and is extended to some extent about the body to provide an approximately circular cross-section to the radiation. The material 3 may be water in one or more flexible bags or may be a viscous or particulate material. The body 1 is retained firmly in a desired position by means such as a retaining strap 4.

The bed 2 and the body 1 are inserted into an aperture 5 in a rotatable member 6 so that a chosen part of the body is centred in the aperture. Bed 2 may include supports on either or both sides of the member 6 but has been shown in FIG. 1 to include supports only at the rear for the sake of clarity. The rotatable member 6 is arranged to rotate about an axis 7, longitudinal of the body and perpendicular to the paper. For that purpose it is supported by three geaar wheels 8a, b, c, which engage with gear teeth, not shown, cut into the periphery of member 6. The gear wheels 8 are journalled in a main frame 9 of the apparatus, which may take any form suitable to support the apparatus and to allow the necessary rotation. A further gear wheel 10, also engaging with the said gear teeth is driven by an electric motor 11, also mounted on the main frame 9 and serves to provide the required rotary motion.

The rotatable member 6 also carries a source 12 of a fan of X-rays, a bank of detectors 13 and a bank of associated collimators 14. The detectors, which in a typical embodiment number 200, can be of any suitable type, for example scintillation crystals with associated photomultipliers or photodiodes.

The source 12 may be of any known type producing a fan shaped spread 15 of x-rays and may be of the type in which the point source of the radiation can be scanned across the surface of the anode to change the position of the fan of x-rays. That shown in FIG. 1 however is fixed in relation to the detectors 13. In this example the source 12 and detectors 17 are substantially equidistant, about 50cm. from axis 7 although this may be varied if desired provided the geometry of the arrangement is accurately known.

In operation source 12 irradiates body 1 with the fan 15 of x-rays. The x-rays are partially absorbed by the body and the intensity after such absorption is measured by detectors 13. Each detector receives radiation transmitted through the body along a respective beam path defined by the dimension of the associated one of collimators 14. The output of each detector is provided to a respective, independent, one of amplifiers 16 where it is amplifed for input to a respective integrator 17. The integrator integrates the signal for a period representing a predetermined degree of rotational motion to provide an analogue signal representing the total intensity of radiation incident on the respective detector in that time and transmitted through the body 1 along a path effectively examined by that detector taking into account the rotational motion. To provide the information regarding the rotation a circular graticule 18 is provided mounted coaxially on the shaft of cog wheel 10. This graticule takes the form of a translucent ring carrying radial engraved lines. The lines can interrupt a light path between a light source and photocell included in a photocell unit 19 mounted on main frame 9. Thus as cog wheel 10 rotates, driving rotary member 6, successive lines interrupt the light path and photocell unit 19 provides pulses at a repetition rate indicative of the rate of the rotary motion. The pulses are provided to integrators 17 for setting and resetting at the desired intervals thus providing the said analogue signals. These signals are converted to digital form in respective analogue/digital converters 20 and to logarithmic form in respective logarithmic converters for output at 22.

The arrangement thus far described is essentially the same as that described in the said U.S. application Ser. No. 476,300 or U.S. application Ser. No. 544,799. The data thus provided at 22 are transmitted to a processing computer, not shown in FIG. 1, for processing to construct the desired representation by any suitable method such as the iterative method described in the said U.S. Pat. or a method employing convolution described in U.S. Pat. No. 3,924,129.

Figure 2:
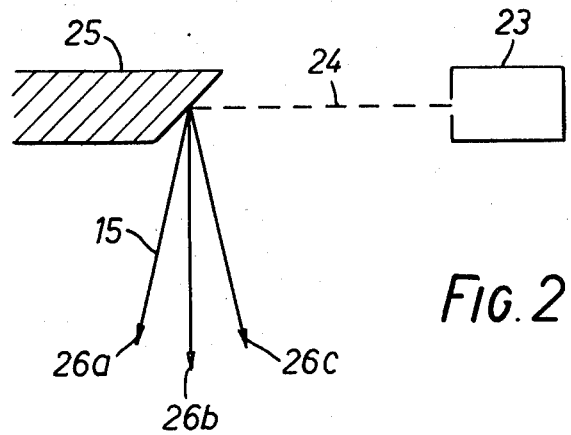
FIG. 2 illustrates the variation of hardness of a fan of radiation from a typical source and FIG. 3 shows in block diagrammatic form a circuit suitable for applying correction factors.

As mentioned hereinbefore, it is known that a fan of x-radiation such as 15 may have a variation in its spectrum with angular position in the fan. The situation is shown in simplified form in FIG. 2 for a fixed anode x-ray tube. An electron gun 23 directs a beam of electrons 24 at a target anode 25 shaped as shown to provide the fan of x-rays 15. In practice the emitted x-rays are not in the fan shown but must be restricted thereto by collimators, not shown. In conventional manner these include two planar sheets of x-ray absorbing material, parallel to the desired plane of the fan and restricting the x-rays thereto. As a result of the varying angle of emission of the x-rays from the target surface, as shown, the x-rays spectrum is variable across the fan. In the example shown the extreme left hand beam, 26a, is relatively hard and the extreme right hand beam 26c is relatively soft compared with the centre beam 26b of fan 15. The arrangement of the present invention accordingly includes a circuit for compensating at least in part for variations of absorption in the body 1 resulting from such variation of x-radiation hardness.

It should be noted that other corrections may also be made to the output signal to provide respective improvements to the final representation of absorption. For example all path lengths of the radiation through body 1 are not equal in view of the approximately circular cross-section of the body and surrounding material. For this reason the outer detectors of the array tend to give high outputs even for a body of uniform absorption. This may be corrected by many means. For example suitably shaped attenuating bodies may be provided to equalise the path lengths or the gains of the respective detectors and/or amplifiers may be appropriately adjusted. Alternatively or in addition correction factors may be measured in the presence of an artificial body of uniform absorption, such as water in a suitably shaped box, or a body phantom of plastic material. Such correction factors may later be subtracted from all readings for the real body 1.

Such subtractive correction factors are not suitable for correcting for variations of hardness of the radiation across the fan 15 since the relationship between the hardness of the radiation and the absorption over a particular path length is not linear. The required compensation is provided by an additional multiplicative operation utilising differential hardness weighting factors. It will be apparent that such factors may be readily calculated by those skilled in the art since the factors governing the spectrum of radiation, emitted by such souces as 12, are well known. However it is also possible to obtain, by measurement, factors sufficient to provide a satisfactory correction for practical purposes. Such measurements are made using output readings obtained by the detectors in the absence of rotary motion in which case the integrators can be controlled by an external pulse generator, not shown. Initially any corrections to be made for path length or other factors are carried out so that the detectors provide substantially equal outputs for a circular phantom body of uniform absorption. This body is then replaced by a similar phantom, not shown, including a bar of material of higher absorption, such as aluminium, carbon, boron etc., substantially perpendicular to the median line of fan 15, further output readings are obtained from the detectors these readings being unequal if hardness variations are signficant. Correction factors are now calculated for each detector such that the outputs, multiplied by respective factors are subtantially equal. Such corrections are approximately correct being accurate only for the phantom used but if the phantom has an absorption close to that for a typical body then the corrections are suitable for all practical purposes.

In the arrangement illustrated for FIG. 1 the radiation intercepted by a single detector is, at all scan times, emitted by source 112 at the same angle to the surface of the anode. However it will be understood that, for any arrangements in which that is not true, appropriate correction factors should be determined for any scan positions in which the hardness distribution changes.

Figure 3:
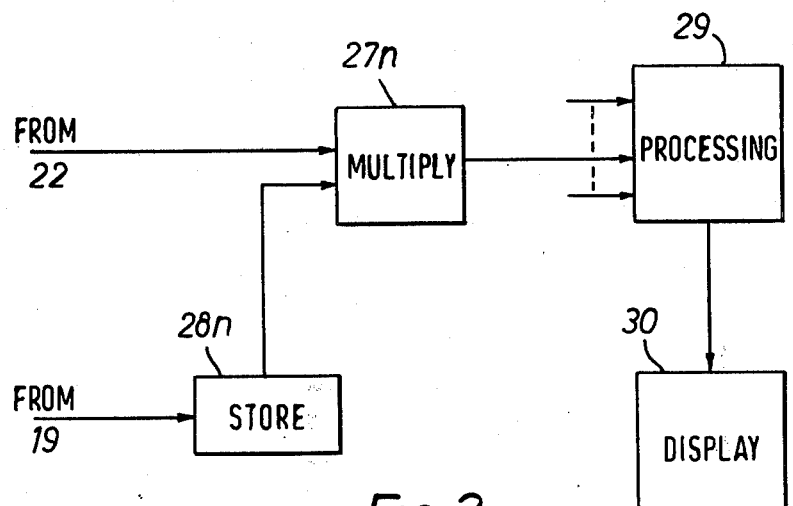

There is shown in FIG. 3 a block diagram of a circuit, for applying the desired corrections. A typical digited output signal originating from one detector may be identified by the subscript $n$. This is derived at 22 from a respective converter 21 of FIG. 1 and is applied to a respective multiplier $27n$. There it is multiplied by an appropriate hardness weighting factor, derived as described hereinbefore and held in a store $28n$. The factor may be withdrawn from store $28n$ for example in response to the pulses from photocell unit 19 or on command of a central control computer, not shown. The multiplied signal is then applied, together with similar signals originating from the other detectors, to a processing computer 29. All such signals derived in the course of, say, 180° rotation are processed therein, as mentioned hereinbefore, for display, on a display unit 30, of the final representation in the form of absorption coefficients, corresponding to individual notional elements of the cross-section of the body being examined, displayed at positions corresponding to the relative positions of those elements in the cross-section. It will be apparent to those skilled in the art that other circuits may readily be devised to apply the corrections.

Although the invention has been described in terms of a fan of radiation subjected only to a rotational motion it will be understood that it is equally applicable to any arrangement using a fan of radiation. Other such arrangements include those in which the source and detectors are also subject to a reciprocating lateral motion in the place of examination.

What I claim is:

1. Medical radiographic apparatus, for examining cross-sectional slices of patients' bodies, comprising means defining a patient position, a source of a fan-shaped distribution of penetrating radiation, comprising a plurality of divergent rays of said radiation, disposed outside said patient position, scanning means for moving said source angularly around said patient position to project said radiation through a predetermined region of said patient position along a plurality of divergent beam paths from each of a series of locations distributed angularly around said patient position, detector means for detecting radiation emergent from said patient position along each of said beam paths to provide electrical output signals indicative of the amounts of radiation so emergent along said paths, processing circuit means for changing the amplitudes of the output signals corresponding to different ones of said divergent rays, from each of said locations, caused by variation of the energy spectrum of radiation propagating at different angles within the distribution and means for combining the changed output signals for a succession of said pluralities of beam paths to form an image of a body slice disposed in said region, said image comprising a pattern of image elements representing absorption coefficients of corresponding notional elements in said body slice for said radiation.

2. A medical diagnostic X-ray machine for examining a patient slice which extends along a planar section through the patient, comprising:

means for generating X-radiation propagating along each beam path of a number of fan-shaped distributions of beam paths, each distribution being made up of a number of beam paths which have one of their ends at a common apex and their other ends distributed along an arc of an orbit extending around the patient and substantially coinciding with said section, the apices of the distribution being distributed along an orbit extending at least half way around the patient and also substantially coinciding with the section, at least some of the beam paths of each fan-shaped distribution passing through said slice of the patient;

means for producing output signals each related to the amount of radiation present at at least one of the ends of each beam path over a selected time interval;

means for deriving a differential hardness correction factor for each of at least a substantial subset of the beam paths making up a fan-shaped distribution of beam paths, said correction factors being a function of variations in the spectrum of the X-radiation with angular position of the beam paths within the fan-shaped distribution; and means for receiving the output signals and the differential hardness correction factors and for forming therefrom a picture element signal corresponding to each of the elements into which the patient slice is divided by a finite Cartesian matrix notionally superimposed on the slice and means for displaying said picture element signal to display thereby a picture of the anatomy of said slice of the patient.

3. A medical diagnostic X-ray machine as in claim 2 in which the means for deriving said differential hardness correction factors comprise means for storing a correction factor for each of the beam paths within a fan-shaped distribution, each different correction factor being associated with a differently positioned beam path within the fan-shaped distribution, and including means for causing said forming means to receive each output signal for a beam path of a distribution coupled with the associated differential hardness correction factor from the storing means, said forming means including means for weighting each received output signals in accordance with the associated differential hardness correction factor and for forming said picture element signal based on the so weighted output signals.

4. A medical diagnostic X-ray machine for examining a patient slice which extends along a planar section through the patient, comprising:

means for generating a beam of X-radiation originating at a radiation origin and propagating therefrom through the patient along a fan-shaped distribution of beam paths which are along the section and are angularly spaced from each other in the distribution;

means for providing differential hardness correction factors related to the individual hardness of the X-radiation along the respective individual beam paths of the fan-shaped distribution;

means for positioning the radiation origin at each of a number of locations distributed along an orbit extending at least half way around the patient to thereby cause said fan-shaped distribution of beam paths to intersect the patient at a number of different angles;

means for deriving an output signal for each of the beam paths of each distribution related to the amount of radiation from the radiation origin which has passed through the patient along the respective beam path;

means for weighting each output signal by the correction factor corresponding to the position within the fan-shaped distribution of the beam path related to the output signal to thereby derive corrected output signals; and means for receiving said corrected output signals and for deriving therefrom a picture element signal for each of the elements into which the patient slice is divided by a finite Cartesian matrix notionally superimposed on the slice and for displaying said picture element signals to thereby display a picture of the anatomy of the patient slice examined with the machine.

* * * * *

UNITED STATES PATENT AND TRADEMARK OFFICE
CERTIFICATE OF CORRECTION

PATENT NO. : 4,118,628

DATED : October 3, 1978

INVENTOR(S) : GODFREY NEWBOLD HOUNSFIELD

It is certified that error appears in the above-identified patent and that said Letters Patent are hereby corrected as shown below:

Claim 2 (Column 5, line 44) delete "distribution" and insert -- distributions --.

Claim 3 (Column 6, line 22) delete "signal" and insert -- signals --.

Signed and Sealed this

Seventeenth Day of April 1979

[SEAL]

Attest:

RUTH C. MASON
Attesting Officer

DONALD W. BANNER
Commissioner of Patents and Trademarks